(12) United States Patent
Teng et al.

(10) Patent No.: US 6,387,942 B2
(45) Date of Patent: May 14, 2002

(54) METHOD OF TREATING DISORDERS RELATED TO PROTEASE-ACTIVATED RECEPTORS-INDUCED CELL ACTIVATION

(75) Inventors: Che-Ming Teng, Taipei; Sheng-Chu Kuo, Taichung; Fang Yu Lee, Tachia Taichung, all of (TW)

(73) Assignee: Yung Shin Pharmaceutical Ind. Co. Ltd, Tachia (TW)

( * ) Notice: Subject to any disclaimer, the term of this patent is extended or adjusted under 35 U.S.C. 154(b) by 0 days.

(21) Appl. No.: 09/883,742

(22) Filed: Jun. 18, 2001

Related U.S. Application Data

(60) Provisional application No. 60/212,408, filed on Jun. 19, 2000.

(51) Int. Cl.[7] ...................... A61K 31/40; A61K 31/405
(52) U.S. Cl. ...................................... 514/414; 514/415
(58) Field of Search ................................. 514/414, 415

(56) References Cited

U.S. PATENT DOCUMENTS 5,574,168 A    11/1996   Kuo et al. ................ 548/360.5

FOREIGN PATENT DOCUMENTS

| EP | 0 667 345 A1 | 8/1995 | |
|---|---|---|---|
| WO | WO 98/16223 | 4/1998 | |
| WO | 2249542 | 10/1998 | ......... C07D/405/04 |

OTHER PUBLICATIONS

"How the protease thrombin talks to cells" by Shaun R. Coughlin. Proc. Natl. Acad. Sci. USA, vol. 96, Sep. 1999, pp. 11023–11027.

"Protease–Activated Receptors and Platelet Function" by Shaun R. Coughlin. ©F. K. Schattauer Verlagsgesellschaft mbH (Stuttgart) 82(2) 353–356 1999.

Effects of the soluble guanylyl cyclase activator, YC–1, on vascular tone, cyclic GMP levels and phosphodiesterase activity by Jan Galle, Ulrike Zabel, Ulrich Hubner, Armin Hatzelmann, Birgit Wagner, Christoph Wanner and Harald H.H.W. Schmidt, British Journal of Pharmacology, vol. 127, 1999. pp. 195–203.

Coughlin et al., "How to protease throbim talks to cells," Proc. Natl. Acad. Sci., 1999, 96, 11023–11027.

Wu et al., "YC–1 inhibited human platelet aggregation through NO–independent activation of soluble guanylate cyclase," British Journal of Pharmacology, 1995, 116, 1973–1978.

Yu et al., "Inhibition of Platelet Function by A 02131–1, a Novel Inhibitor of cGMP–Specific Phosphodiesterase, In Vitro and In Vivo," Blood, 1996, 87, 3758–3767.

Ko et al., "YC–1, a Novel Activator of Platelet Guanylate Cyclase," Blood, 1994, 84, 4226–4233.

*Primary Examiner*—Raymond Henley, III
(74) *Attorney, Agent, or Firm*—Fish & Richardson, P.C

(57) ABSTRACT

A method of treating a disorder related to cell activation induced by protease-activated receptors. The method includes administering to a subject in need thereof a compound having a pyrazolyl core; an aryl group, via an via an alkylene linker, bonded to 1-N of the pyrazolyl core; a second aryl group fused at 4-C and 5-C of the pyrazolyl core; and a third aryl group bonded directly to 3-C of the pyrazolyl core.

30 Claims, No Drawings

METHOD OF TREATING DISORDERS RELATED TO PROTEASE-ACTIVATED RECEPTORS-INDUCED CELL ACTIVATION

CROSS-REFERENCE TO RELATED APPLICATION

Pursuant to 35 U.S.C. § 119(e), this application claims the benefit of prior U.S. provisional application 60/212,408, filed Jun. 19, 2000.

BACKGROUND OF THE INVENTION

Thrombin, a coagulation protease, activates G protein-coupled protease-activated receptors (PARs) which in turn induce cell activation such as platelet aggregation and proliferation of vascular smooth vessel cells. See Coughlin, Proc. Natl. Acad. Sci. USA, 1999, 96: 11023–11027. Aggregation of the activated platelets contributes to pathogenesis of many diseases, e.g., atherosclerosis, myocardial infarction, unstable angina pectoris, and thrombosis. It is therefore desirable to discover a drug which can treat such diseases by specifically inhibiting the activation of PARs, e.g., by means of inhibiting thrombin.

SUMMARY OF THE INVENTION

This invention relates to a method of treating a disorder related to PAR-induced platelet aggregation. The method includes administering to a subject -n need thereof a compound having a pyrazolyl core and three aryl groups: (1) a first aryl group, via an alkylene linker, bonded to 1-N of the pyrazolyl core, (2) a second aryl group fused at 4-C and 5-C of the pyrazolyl core, and (3) a third aryl group bonded directly to 3-C of the pyrazolyl core. Each of these three aryl groups, independently, is phenyl, thienyl, furyl, or pyrrolyl, which is optionally mono-substituted or multi-substituted with halo (e.g., —Cl), alkyl (e.g., —$C_5H_{11}$), carboxyl, alkoxycarbonyl [e.g., —(C=O)—O—$C_5H_{11}$], thiocarbonyl [e.g., —(C=O)—S—$C_4H_9$], aminocarbonyl [e.g., —(C=O)—N($C_3H_7$)$_2$], hydroxyalkyl (e.g., —$C_6H_{12}$OH), alkoxyalkyl (e.g., —$C_3H_6$—O—$^iC_4H_9$), amino, aminoalkyl [e.g., —$C_3H_6$N($C_3H_7$)$_2$], thioalkyl (e.g., —$C_4H_8$S$C_4H_9$), or oxyalkoxy (e.g., —OCH$_2$CH$_2$O— as a disubstituent). The compound is administered to the subject in an amount effective for treating the disorder, Shown below is a formula which encompasses a number of the fused pyrazolyl compounds described above:

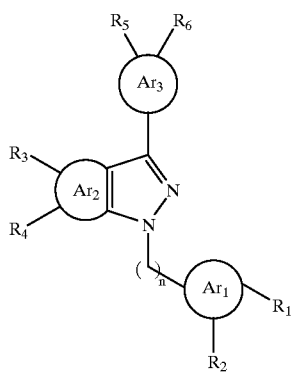
(I)

Formula (I) includes a pyrazolyl core and three aryl groups, i.e., $Ar_1$, $Ar_2$, and $Ar_3$, as the three aryl groups described above. Each of $Ar_1$, $Ar_2$, and $Ar_3$, independently, is phenyl, thienyl, furyl, or pyrrolyl; each of $R_1$, $R_2$, $R_3$, $R_4$, $R_5$, and $R_6$, independently, is H, halo, —R, —C(=O)OH, —C(=O)OR, —C(=O)SH, —C(=O)SR, —C(=O)NRR', —ROH, —ROR', —RSH, —OR, —OH, —SR, —SH, —NRR', —NHR, —RNR'R", —RNHR', or —RSR', or $R_1$ and $R_2$ together, $R_3$ and $R_4$ together, or $R_5$ and $R_6$ together, are —ORO—, wherein each of R, R', and R", independently, is $C_{1-4}$alkyl; and n is 1, or 2, or 3.

A subset of the compounds of formula (I) are featured by that n is 1, $Ar_3$ is phenyl, and each of $R_5$ and $R_6$, independently, is H, halo, —R, —C(=O)OH, —C(=O)OR, —C(=O)SH, —C(=O)SR, —C(=O)NRR', —ROH, —ROR', —RSH, —NRR', —NHR, —RNR'R", —RNHR', or —RSR', or $R_5$ and $R_6$ together are —ORO—.

Another subset of the compounds of formula (I) are featured by that n is 1, $Ar_3$ is furyl, and each of $R_5$ and $R_6$, independently, is H, halo, —R, —C(=O)OH, —C(=O)OR, —C(=O)SH, —C(=O)SR, —C(=O)NRR', —ROH, —ROR', —RSH, —NRR', —NHR, —RNR'R", —RNHR', or —RSR', or $R_5$ and $R_6$ together are —ORO—.

Set forth below are some specific examples of the compounds which can be used to practice the method of this invention: 1-benzyl-3-(3'-ethoxycarbonyl)phenyl-indazole, 1-benzyl-3-(3'-hydroxymethyl)phenyl-indazole, 1-benzyl-3-(5'-diethylaminomethyl)-furyl-indazole, 1-benzyl-3-(5'-methoxymethyl)furyl-indazole, 1-benzyl-3-(5'-hydroxymethyl)furyl-6-methyl-indazole, 1-benzyl-3-(5'-hydroxymethyl)-furyl-indazole, 1-benzyl-3-(5'-hydroxymethyl)-furyl-6-fluoro-indazole, 1-benzyl-3-(5'-hydroxymethyl)-furyl- 6-methoxy-indazole, and 1-benzyl-3-(5'-hydroxymethyl)-furyl-5, 6-methylenedioxo-indazole.

The structures of 1-benzyl-3-(3'-ethoxycarbonyl)phenyl-indazole and 1-benzyl-3-(5'-diethylaminomethyl)-furyl-indazole are shown below with the atoms on the aryl groups numbered:

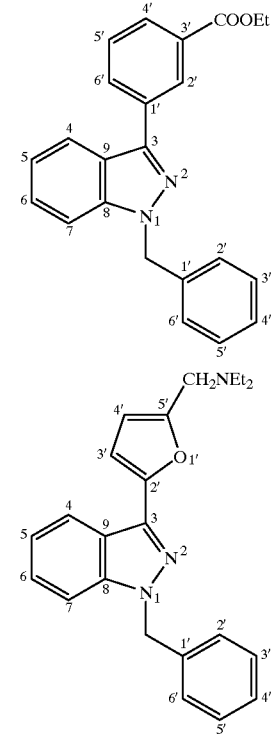

For brevity, the fused pyrazolyl compounds described above include their pharmaceutically acceptable salts and prodrugs, if applicable. Such a salt can be formed between a positively charged substituent (e.g., amino) in a fused pyrazolyl compound and a negatively charged counterion (e.g., chloride, bromide, iodide, sulfate, nitrate, phosphate, or acetate). Likewise, a negatively charged substituent (e.g., carboxylate) in a fused pyrazolyl compound can form a salt with a positively charged ion (e.g., sodium ion, potassium ion, magnesium ion, calcium ion, or an ammonium cation such as tetramethylammonium ion). Examples of the salts that can be used in the method of this invention include a hydrochloride salt of 1-benzyl-3-(5'-aminomethyl)furyl-indazole and a sodium salt of 1-benzyl-3-(3'-carboxyl)phenyl-indazole. Examples of the prodrugs include esters and other pharmaceutically acceptable derivatives, which, upon administration to a subject, are capable of providing fused pyrazolyl compounds described above.

A fused pyrazolyl compound is formulated into a pharmaceutical composition before it is administered to a subject in need of treatment of a disorder related to PAR-induced cell activation (e.g., atherosclerosis, myocardial infarction, unstable angina pectoris and thrombosis). Thus, also within the scope of the invention is the composition which contains an effective amount of the compound (or its salt) and a pharmaceutically acceptable carrier for use in treating a disorder or disease aforementioned. Examples of the carriers include colloidal silicon dioxide, magnesium stearate, cellulose, sodium lauryl sulfate, and D&C Yellow# 10. The invention also relates to the use of such a composition for the manufacture of a medicament for the treatment of above-mentioned disorders or diseases.

It was unexpected that the method of this invention specifically inhibits PAR-induced cell activation, e.g., platelet aggregation, with no or little inhibitory effect on that induced by other platelet activators. Other advantages or features of the invention will be apparent from the following detailed description of several embodiments, and also from the appending claims.

DETAILED DESCRIPTION OF THE INVENTION

This invention relates to using a fused pyrazolyl compound to treat a disorder caused by PAR-induced cell activation.

A method of synthesizing the fused pyrazolyl compound is as follows: An aryl aryl ketone is first prepared by coupling an arylcarbonyl chloride with another aryl compound. Each aryl compound is optionally mono- or multi-substituted. The ketone then reacts with an arylalkylhydrazine, the aryl group of which is also optionally mono- or multi-substituted, to form a hydrazone containing three aryl groups. The hydrazone is transformed into a fused pyrazolyl compound. In the fused pyrazolyl compound, an aryl group is connected to 1-N of the pyrazolyl core via an alkylene linker, another aryl group is fused at 4-C and 5-C of the pyrazolyl core, and the third aryl group is directly connected to 3-C of the pyrazolyl core. Derivatives of the fused pyrazolyl compound may be obtained by modifying the substituents on any of the aryl groups.

Synthesis of three types of fused pyrazolyl compounds, i.e., 1-benzyl-3-furyl-indazole, 1-benzyl-3-phenyl-indazole, and thienylpyrazole.

Shown in Scheme 1 below is a method of synthesizing five 1-benzyl-3-furyl-indazole compounds, indicated as (1)–(5), all of which can be used to practice the method of the invention.

Scheme 1

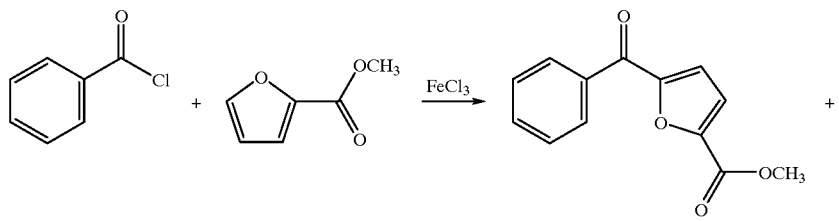

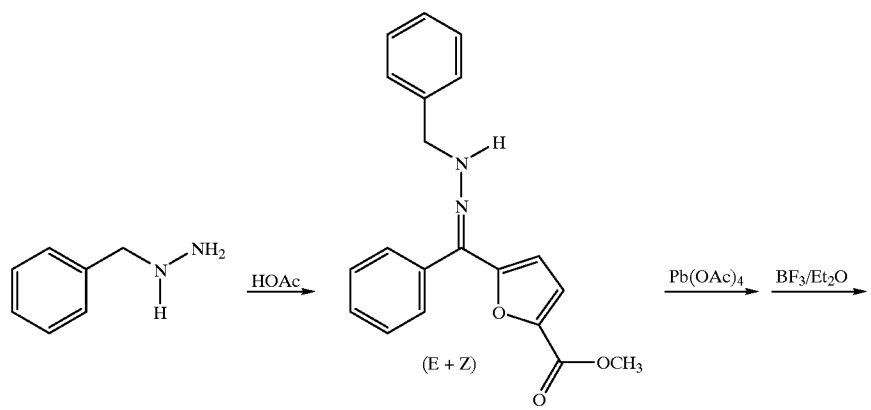

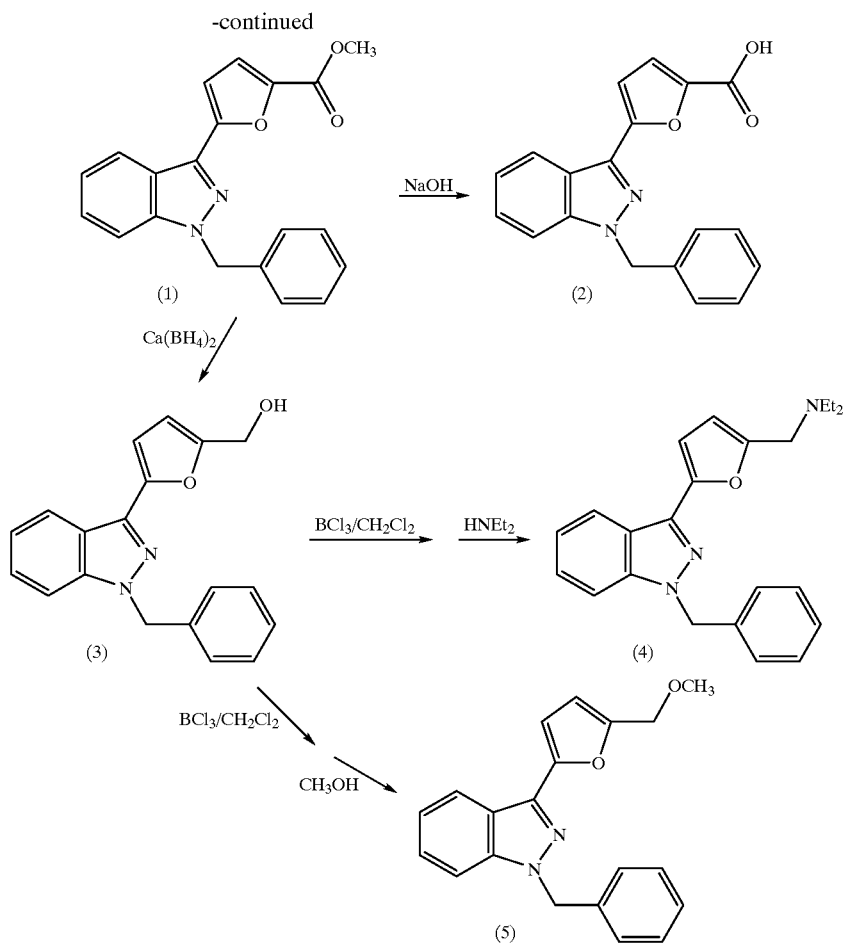

As shown in Scheme 1,5'-methoxycarbonyl-2-furyl phenyl ketone, prepared by coupling methyl 2-furoate with benzoyl chloride, reacts with benzylhydrazine to form a benzylhydrazone as a mixture of E- and Z-form isomers. The isoform mixture is then treated with a mixture of Pb(OAc)$_4$ and BF$_3$/Et$_2$O in CH$_2$Cl$_2$ at room temperature, via a same azo intermediate, to give compound (1). The methoxycarbonyl group in compound (1) can be hydrolyzed with NaOH to carboxylic acid group to form compound (2). Alternatively, the methoxycarbonyl group can be reduced with Ca(BH$_4$)$_2$ in THF to hydroxymethyl group to form compound (3). Compound (3) can be successively treated with BCl$_3$ and diethylamine to obtain an N,N-diethylaminomethyl derivative, i.e., compound (4). Optionally, compound (3) can also be successively treated with BCl$_3$ and methanol to obtain a methoxymethyl derivative, i.e., compound (5). Although not shown in the scheme, derivatives of compounds (1)–(5) can be obtained by using other 2-furoates, benzoyl chlorides, or benzylhydrazones, in which the aryl group is mono- or multi-substituted.

1-Benzyl-3-phenyl-indazole compounds can be prepared by following the reaction procedure shown in Scheme 1 except that benzophenone, optionally mono- or multi-substituted, is used instead of 2-furyl phenyl ketone. As an initial step, benzophenone is oxidized with CrO$_3$ to form benzoylbenzoic acid. The benzoylbenzoic acid is then treated with ethanol to form ethyl benzoylbenzoate, which can be transformed into 1-benzyl-3-phenyl-indazole. 1-Benzyl-3-phenyl-indazole can be further transformed into its derivatives by modifying the substituent(s) on the three aryl groups, if applicable.

Fused pyrazolyl compounds containing a thienopyrazole moiety can also be prepared by following the synthetic method shown in Scheme 1, except that 2-thienyl aryl ketone is used instead of 2-furyl phenyl ketone. The mono- or multi- substitutents, if any, of the thienopyrazolyl compounds thus obtained, can be further modified to afford additional thienopyrazolyl compounds.

An effective amount of a fused pyrazolyl compound or its salt is formulated with a pharmaceutically acceptable carrier to form a pharmaceutical composition before administered to a subject in need of treatment of a disorder related to PAR-induced platelet aggregation. "An effective amount" refers to the amount of the compound which is required to confer therapeutic effect on the treated subject. The interrelationship of dosages for animals and humans (based on milligrams per meter squared of body surface) is described by Freireich et al., Cancer Chemother. Rep., 1966, 50, 219. Body surface area may be approximately determined from height and weight of the patient. See, e.g., Scientific Tables, Geigy Pharmaceuticals, Ardley, New York, 1970, 537. Effective doses will also vary, as recognized by those skilled in the art, depending on the route of administration, excipient usage, and possibility of co-usage with other therapeutic treatments including use of other anti-platelet aggregation agents.

The pharmaceutical composition may be administered via a parenteral route, e.g., topically, subcutaneously, intraperitoneally, intramuscularly, and intravenously. Examples of parenteral dosage forms include aqueous solutions of the active compound, in an isotonic saline, 5% glucose, or any other well-known pharmaceutically acceptable carrier. Solubilizing agents, such as cyclodextrins, or other solubilizing agents well known to those familiar with the art, can also be included in the pharmaceutical composition.

A fused pyrazolyl compound to be used to practice the method of the invention can be formulated into dosage forms for other routes of administration (e.g., orally, mucosally, or percutaneously) utilizing well-known methods. The pharmaceutical composition can be formulated, for example, in dosage forms for oral administration in a capsule, a gel seal, or a tablet. Capsules may comprise any well-known pharmaceutically acceptable material such as gelatin or cellulose derivatives. Tablets may be formulated in accordance with the conventional procedure by compressing mixtures of the active compounds, a solid carrier, and a lubricant. Examples of solid carriers include starch and sugar bentonite. The compound can also be administered in a form of a hard shell tablet or capsule containing, for example, lactose or mannitol as a binder, a conventional filler, and a tableting agent.

A suitable in vitro inhibition assay can be used to preliminarily evaluate a fused pyrazolyl compound's ability to inhibit cell activation induced by PARs, which are pre-activated by thrombin. For example, a platelet suspension in Tyrode's solution can be prepared and incubated with a compound to be tested, thrombin added to trigger platelet aggregation, and the aggregation measured turbidimetrically with a light-transmission aggremometer. In vivo screening can be performed by following procedures well known in the art.

Without further elaboration, it is believed that one skilled in the art can, based on the description herein, utilize the present invention to its fullest extent. All publications recited herein are hereby incorporated by reference in their entirety. The following specific examples, which describe synthesis and biological testing of various compounds that can be used to practice the method of this invention, are therefore, to be construed as merely illustrative, and not limitative of the remainder of the disclosure in any way whatsoever.

EXAMPLE 1

Synthesis of 1-Benzyl-3-(5'-methoxycarbonyl-2'-furyl)indazole (a) Synthesis of 5-Methoxycarbonyl-2-furyl Phenyl Ketone Anhydrous ferric chloride (0.42 g, 2.6 mmole) and benzoyl chloride (29.6 g, 0.21 mole), were dissolved in $CCl_4$ (40 mL) and added dropwise over 10 min with methyl-2-furoate (25.2 g, 0.20 mmole). The reaction mixture was then heated under reflux for 36 hours, and after cooling was added with water (120 mL). The mixture was stirred for 1 hour and then allowed to sit until it separated into two layers. The water layer and precipitate were extracted with chloroform. The chloroform extract was dried over anhydrous magnesium sulfate and then filtered. The solvent of the filtrate was removed under a reduced pressure; the residue was recrystallized from isopropanol to afford 28.4 g 5-methoxycarbonyl-2-furyl phenyl ketone in a yield of 65.0%.

mp: 70–73° C. MS (%), m/z: 230 ($M^+$). IR (KBr) $\gamma_{max}$: 1720, 1650 $cm^{-1}$(C=O). $^1$H-NMR ($CDCl_3$, 200 MHz) δ: 3.86 (3H, s, —$CH_3$), 7.26–7.32 (2H, m, H-3',5'), 7.40–7.65 (3H, m, H-3,4,4'), and 8.05–8.10 (2H, m, H-2', 6').

(b) Synthesis of 1-Benzyl-3-(5'-methoxycarbonyl-2'-furyl)indazole

5-Methoxycarbonyl-2-furyl phenyl ketone (5.5 g, 0.024 mole) was dissolved in methanol (60 mL), added with benzylhydrazine (9 g, 0.07 mole) and acetic acid (0.5 mL) and then heated under reflux till the reaction was completed. After cooling, the solvent was evaporated. The resultant residue was extracted with chloroform and washed with dilute HCl solution, then water, and then dried over anhydrous magnesium sulfate and filtered. The solvent of the filtrate was removed to give 5-methoxycarbonylfuryl phenyl ketone benzylhydrazone.

A solution of hydrazone thus obtained in dichloromathane (100 mL) was added dropwise to the solution of $Pb(OAc)_4$ (28.2g, 0.06 mole) in dichloromethane (400 mL). After addition, the mixture was allowed to react at 30±2° C. for 30 min, and $BF_3.Et_2O$ (containing 47% of $BF_3$, 122 mL) was added. The mixture was heated under reflux for 30 min and then poured into ice water (1000 mL) to terminate the reaction. The organic layer was separated and washed sequentially with water and 10% sodium carbonate solution, then neutralized by water wash. It was dried over anhydrous magnesium sulfate and was concentrated under vacuum to an oily crude product. Ethanol was then added to the crude product, and the mixture was allowed to precipitate by freeze overnight. The solid precipitate was collected and recrystallized from ethanol to give 3.7 g 1-benzyl-3-(5'-methoxycarbonyl-2'-furyl)indazole in a yield of 47.0%.

mp: 117–118° C. MS (%), m/z: 332 ($M^+$). IR (KBr) $\gamma_{max}$: 1720 $cm^{-1}$(C=O). $^1$H-NMR ($CDCl_3$) δ: 3.95 (3H, s, $CH_3$), 5.66 (2H, s, =$NCH_2$—), 7.02 (1H, d, J=3.5 Hz, H-3'), 7.20–7.40 (9H. m, H-5, 6, 7, 4', phenyl), and 8.26 (1H, dd, J=8.1, 1.5 Hz, H-4).

EXAMPLE 2

Synthesis of 1-Benzyl-3-(5'-methoxycarbonyl-2'-furyl)-6-fluoroindazole

4'-Fluorophenyl 5-methoxycarbonyl-2-furyl ketone (5.96 g, 24 mmole) was prepared as in Example 1 (a), and used as the starting material to obtain 4.1 g 1-benzyl-3-(5'-methoxycarbonyl-2'-furyl)-6-fluoroindazole in a yield of 48.8%, according to the procedure described in Example 1 (b).

mp: 108–109° C. MS (%), m/z: 350 ($M^+$). IR (KBr) $\gamma_{max}$: 1710 $cm^{-1}$(C=O). $^1$H-NMR (DMSO-$d_6$, 200 MHz) δ: 3.87 (3H, s, —$CH_3$), 5.73 (2H, s, =$NCH_2$—), 7.18–7.37 (7H, m, H-5,3', phenyl), 7.45 (1H, d, J=3.5 Hz, H-4),7.77 (1H, dd, J=10.0, 1.5 Hz, C7-H), and 8.17 (1H. dd, J=8.0, 6.3 Hz, C4-H).

EXAMPLE 3

Synthesis of 1-Benzyl-3-(5-methoxycarbonyl-2'-furyl)-6-methylindazole

5-Methoxycarbonyl-2-furyl 4'-methylphenyl ketone (5.85 g, 0.024 mole) was similarly prepared and used as the starting material to obtain 3.7 g 1-benzyl-3-(5-methoxycarbonyl-2'-furyl)-6-methylindazole in a yield of 45.1 %.

mp: 102–104° C. MS (%), m/z: 346 ($M^+$) IR (KBr) $\gamma_{max}$: 1720 $cm^{-1}$(C=O). $^1$H-NMR(DMSO-$d_6$) δ: 2.46 (3H, s, —$CH_3$), 3.87 (3H, s, —$OCH_2$—), 5.71 (2H, s, =$NCH_2$—), 7.14–7.36 (7H, m, H-5, 3", phenyl), 7.45 (1H, d, J=3.4 Hz, H-4); 7.59 (1H, s, H-7); and 8.10 (1H, d. J=8.0 Hz, H-4).

EXAMPLE 4

Synthesis of 1-Benzyl-3-(5'-methoxycarbonyl-2'-furyl)-6-methoxyindazole

5-Methoxycarbonyl-2-furyl 4'-methoxylphenyl ketone (6.24 g. 0.024 mole) was similarly prepared and used as the starting material to obtain 4.4 g 1-benzyl-3-(5'-methoxycarbonyl-2'-furyl)-6-methoxyindazole in a yield of 50.2%.

mp: 108–109° C. MS (%), m/z: 362 (M$^+$). IR (KBr) $\gamma_{max}$: 1710 cm$^{-1}$(C=O). $^1$H-NMR (DMSO-d$_6$, 200 MHz) δ: 3.85 (3H, s, —OCH$_3$), 3.88 (3H, s, —COOCH$_3$), 5.71 (2H, s, =NCH$_2$—), 6.95 (1H, d, J=8.5 Hz, H-5), 7.16 (1H, d. J=3.5 Hz, H-3'), 7.24–7.36 (6H, m, H-7, phenyl), 7.40 (1H, d, J=3.5 Hz, H-4), and 7.98 (1H, d, J=8.5 Hz, H-4).

EXAMPLE 5

Synthesis of 1-Benzyl-3-(5'-methoxycarbonyl-2'-furyl)-5,6-methylenedioxoindazole 5-Methoxycarbonyl-2-furyl-3', 4'-methylenedioxophenyl ketone (6.6 g. 0.024 mole) was similarly prepared and used as the starting material to obtain 5.7 g 1-benzyl-3-(5'1-methoxycarbonyl-2'furyl)-5,6-methylenedioxoindazole in a yield of 63.8%.

mp: 190–192° C. MS (%), m/z: 376 (M$^+$). IR (KBr) $\gamma_{max}$: 1724 cm$^{-1}$(C=O). $^1$H-NMR (CDCl$_3$, 200 MHz) δ: 3.93 (3H, s, —OCH$_3$), 5.51 (2H, s, =NCH$_2$—), 5.98 (2H, s, —OCH$_2$O—), 6.62 (1H, s, H-7), 6.91 (1H, d, J=3.8 Hz, H-3'), 7.18–7.32 (6H, m, H-4', phenyl), and 7.52 (1H, s, H-4).

EXAMPLE 6

Synthesis of 1-Benzyl-3-(5'-hydroxycarbonyl-2'-furyl)indazole

1-Benzyl-3-(5'-methoxycarbonyl-2 '-furl)indazole (100 mg, 0.32 mmole) was dissolved in a mixture of methanol (8 mL) and sodium hydroxide solution (75 mg in 3 mL water) then heated under reflux. After cooling, the solvent was removed under a reduced pressure. The residue was dissolved in water (1.5 mL), and the aqueous solution was acidified with a diluted HCl solution to generate a crystal. The crystal was collected, and then recrystallized from acetone to obtain 73 mg 1-benzyl-3-(5'-hydroxycarbonyl-2'-furyl)indazole in a yield of 71.7%.

mp: 202–203° C. MS (%), m/z: 318 (M$^+$). IR (KBr) $\gamma_{max}$: 3450 cm$^{-1}$(—OH) and 1700 cm$^{-1}$(C=O). $^1$H-NMR (DMSO-d$_6$, 200 MHz) δ: 5.76 (2H, s, =NCH$_2$—), 7.20 (1H, d, J=3.5 Hz, H-3'), 7.26–7.35 (6H, m, H-5, phenyl), 7.38 (1H, d, J=3.5 Hz, H-4'), 7.49 (1H, t, J=8.2 Hz, H-6), 7.80 (1H, dd, J=8.2, 1.5 Hz, H-7), and 8.15 (1H, d, J=8.1, 1.5 Hz, H-4).

EXAMPLE 7

Synthesis of 1-Benzly-3-(5'-hydroxycarbonyl-2'-furyl)-6-fluoroindazole

1-Benzyl-3-(5'-methoxycarbonyl-2'-furyl)-6-fluoroindazole (112 mg, 0.32 mmole) was used as the starting material and treated according to the procedure described in Example 6 to obtain 70 mg 1-benzyl-3-(5'-hydroxycarbonyl-2'-furyl)-6-fluoroindazole in a yield of 65%.

mp: 252–253° C. MS (%), m/z: 336 (M$^+$). IR (KBr) $\gamma_{max}$: 3450 cm$^{-1}$(—OH) and 1690 cm$^{-1}$(C=O). $^1$H-NMR (DMSO-d$_6$, 200 MHz) δ: 5.72 (2H, s, =NCH$_2$—), 7.21 (1H, d, J=3.5 Hz, H-3), 7.23–7.33 (6H, m, H-5, phenyl), 7.39 (1H, d, J=3.5 Hz, H-4), 7.79 (1H, dd, J=9.8, 18 Hz, H-7), and 8.17 (1H, dd, J=8.5, 5.3 Hz, H-4).

EXAMPLE 8

Synthesis of 1-Benzyl-3-(5-hydroxycarbonyl-2'-furyl)-6-methylindazole

1-Benzyl-3-(5'-methoxycarbonyl-2'-furyl)-6-methylindazole (111 mg, 0.32 mmole) was used as the starting material and treated according to the procedure described in Example 6 to obtain 95 mg 1-benzyl-3-(5-hydroxycarbonyl-2'-furyl)-6-methylindazole in a yield of 89%.

mp: 201–202° C. MS (%), m/z: 332 (M$^+$). IR (KBr) $\gamma_{max}$: 3450 cm$^{-1}$(—OH), 1700 cm$^{-1}$(C=O). $^1$H-NMR (DMSO-d$_6$, 200 MHz) δ: 2.46 (3H, s, —CH$_3$), 5.70 (2H, s, =NCH$_2$—), 7.16(1H, d, J=3.5 Hz, H-3'), 7.23–7.33 (6H, m, H-5, phenyl), 7.38 (1H, d, J=3.5 Hz, H-4), 7.61 (1H, d, J=1.4 Hz, H-7), and 8.00 (1H, d, J=8.2 Hz, H-4).

EXAMPLE 9

Synthesis of 1-Benzyl-3-(5'-hydroxycarbonyl-2'-furyl)-6-methoxyindazole

1-Benzyl-3-(5'-methoxycarbonyl-2'-furyl)-6-methoxyindazole (116 mg, 0.32 mmole) was used as the starting material and treated according to the procedure described in Example 6 to obtain 88.1 mg 1-benzyl-3-(5'-hydroxycarbonyl-2'-furyl)-6-methoxyindazole in a yield of 77.3%.

mp: 222–223° C. MS (%), m/z: 348 (M$^+$) IR (KBr) $\gamma_{max}$: 3450 cm$^{-1}$(—OH) and 1710 cm$^{-1}$(C=O) $^1$H-NMR (DMSO-d$_6$, 200 MHz) δ: 3.84 (3H, s, —OCH$_3$), 5.70 (2H, s, =NCH$_2$—), 6.95 (1H, dd, J=8.3, 1.8 Hz, H-3'), 7.12 (1H, d, J=3.4 Hz, H-3), 7.25–7.38 (7H, m, H-7,4, phenyl), and 7.98 (1H, d, J=8.3 Hz, H-4).

EXAMPLE 10

Synthesis of 1-Benzyl-3-(5'-hydroxycarbonyl-2'-furyl)-5,6-methylenedioxoindazole 1-Benzyl-3-(5'-methoxycarbonyl-2'-furyl)-5,6-methylenedioxoindazole (120 mg, 0.32 mmole) was used as the starting material and treated according to the procedure described in Example 6 to obtain 87.5 mg 1-benzyl-3-(5'-hydroxycarbonyl-2'-furyl)-5,6-methylenedioxoindazole in a yield of 75.5%.

mp: 291–292° C. MS (%), m/z: 362 (M$^+$) IR (KBr) $\gamma_{max}$: 3479 cm$^{-1}$(—OH) and 1720 cm$^{-1}$(C=O) $^1$H-NMR (DMSO-d$_6$, 200 MHz) δ: 5.62 (2H, s, =NCH$_2$—), 6.11 (2H, s, —OCH$_2$O—), 7.09 (1H, d, J=3.6, H-3'), 7.20–7.36 (7H, m, H-7, 4', phenyl), and 7.43 (1H, s, H-4).

EXAMPLE 11

Synthesis of 1-Benzyl-3-(5'-hydroxymethyl-2'-furyl)indazole

Calcium borohydride was first prepared by stirring anhydrous calcium chloride (88.8 mg, 0.8 mmole) with sodium borohydride (60 mg, 1.6 mmole) in anhydrous THF (20 mL) for 4 hours. Then a 30 mL THF solution containing 88.0 mg 1-benzyl-3-(5'-methoxycarbonyl-2'-furyl)indazole (0.27 mmole) was added dropwise to the calcium borohydride solution at 30±2° C. The mixture was heated under reflux for 6 hours, cooled, quenched into crushed ice, placed at a reduced pressure to remove THF, and filtered to obtain a solid product. The solid was extracted with dichloromethane. The extract was concentrated to 50 mL and a solid precipitated after petroleum ether was added. The precipitate was collected and purified by column chromatography (silica gel-benzene) to obtain 70.0 mg 1-benzyl-3-(5'-hydroxymethyl-2'-furyl)indazole in a yield of 87%.

mp: 108–109° C. MS (%), m/z: 304 (M$^+$). IR (KBr) $\gamma_{max}$: 3350 cm$^{-1}$(—OH). $^1$H-NMR (DMSO-d$_6$, 200 MHz) δ: 4.51

(2H, d, J=5.5 Hz, —H$_2$O—), 5.31 (1H, t, J=5.5 Hz, —OH), 5.70 (2H, s, =NCH$_2$—), 6.48 (1H, d, J=3.4 Hz, H-4'), 6.97 (1H, d, J=3.4 Hz, H-3'), 7.21–7.31 (6H, m, H-5, phenyl), 7.45 (1H, t, J=8.2 Hz, H-6), 7.75 (1H, dd, J=8.2, 1.8 Hz, H-7), and 8.12 (1 H. dd, J=8.2. 1.0 Hz. C4-H).

EXAMPLE 12

Synthesis of 1-Benzyl-3-(5'-hydroxymethyl-2'-furyl)-6-fluoroindazole

1-Benzyl-3-(5'-methoxycarbonyl-2'-furyl)-6-fluoroindazole (93 mg, 0.27 mmole) was used as the starting material and treated according to the procedure described in Example 11 to obtain 75.0 mg 1-benzyl-3-(5'-hydroxymethyl-2'-furyl)-6-fluoroindazole in a yield of 88.0%.

mp: 110–112° C. MS (%), m/z; 322 (M$^+$). IR (KBr) $\gamma_{max}$: 3450 cm$^{-1}$(—OH). $^1$H-NMR (DMSO-d$_6$, 200 MHz) δ: 4.49 (2H, br, —CH$_2$O—), 5.45 (1H, br, —OH), 5.88 (1H, s, =NCH$_2$—), 6.48 (1H, d, J=3.2 Hz, H-4'), 6.98 (1H, d, J=3.2 Hz, H-3'), 7.10–7.18 (1H, m, H-7),7.24–7.36 (5H, m, phenyl-H), 7.70 (1H, dd, J=10.0, 2.0 Hz, C5-H), and 8.15 (1H, dd, J=8.5, 5.1 Hz, H-4).

EXAMPLE 13

Synthesis of 1-Benzyl-3-(5'-hydroxymethyl-2'-furyl)-6-methylindazole

1-Benzyl-3-(5'-methoxycarbonyl-2'-furyl)-6-methylindazole (92 mg. 0.27 mmole) was used as the starting material and treated according to the procedure described in Example 11 to obtain 74.0 mg 1-benzyl-3-(5'-hydroxymethyl-2'-furyl)-6-methylindazole in a yield of 88%.

mp: 112–114° C. MS (%), m/z: 318 (M$^+$). IR (KBr) $\gamma_{max}$: 3400 cm$^{-1}$(—OH). $^1$H-NMR (DMSO-d$_6$, 200 MHz) δ: 2.44 (3H, s, —CH$_3$), 4.50 (2H, d. J=5.2 Hz, —CH$_2$O—), 5.30 (1H, br, —OH), 5.64 (2H, s, =NCH$_2$—), 6.45 (1H, d, J=3.3 Hz, H-4'), 6.07 (1H, d, J=3.3 Hz, H-3'), 7.08 (1H, dd, J=8.3, 1.0 Hz, H-5), 7.19–7.36 (5H, m, phenyl-H), 7.57 (1H, d, J=1.0 Hz, H-7), and 7.98 (1H, dd, J=8.3, 1.0Hz, H-4).

EXAMPLE 14

Synthesis of 1-Benzyl-3-(5'-hydroxymethyl-2'-furyl)-6-methoxyindazole

1-Benzyl-3-(5'-methoxycarbonyl-2'-furyl)-6-methoxyindazole (96 mg, 0.27 mmole) was used as the starting material and treated according to the procedure described in Example 11 to obtain 80 mg 1-benzyl-3-(5'-hydroxymethyl-2'-furyl)-6-methoxyindazole in a yield of 90.0%.

mp: 109–110° C. MS (%), m/z: 334 (M$^+$). IR (KBr) $\gamma_{max}$: 3300–3400 cm$^{-1}$(—OH). $^1$H-NMR (CDCl$_3$, 200 MHz) δ: 1.90 (1H, br, —OH), 3.80 (3H, s, —CH$_3$), 4.74 (2H, d, J=2.0 Hz, Hz, —CH$_2$O—), 5.59 (2H, s, =NCH$_2$—), 6.47 (1H, d, J=3.2 Hz, H-4'), 6.59 (1H, d, J=2.0 Hz, H-7), 6.84 (1H, d, J=3.2, 1.0 Hz, H-3'), 6.88 (1H, dd, J=8.5, 1.5 Hz, H-5), 7.17–7.31 (5H, m, phenyl-H), and 7.91 (1H, d. J=8.5 Hz, H-4).

EXAMPLE 15

Synthesis of 1-Benzyl-3-(5'-hydroxymethyl-2'-furyl)-5,6-methylenedioxoindazole

1-Benzyl-3-(5 '-methoxycarbonyl-2'-furyl)-5,6-methylenedioxoindazole (101 mg, 0.27 mmole) was used as the starting material and treated according to the procedure described in Example 11 to obtain 84.5 mg 1-benzyl-3-(5'-hydroxymethyl-2'-furyl)-5,6-methylenedioxoindazole in a yield of 90%.

mp: 122–123° C. MS (%), m/z: 348 (M$^+$). IR (KBr) $\gamma_{max}$: 3387 cm$^{-1}$(—OH). $^1$H-NMR (CDCl$_3$) δ: 2.05 (1H, br, —OH), 4.71 (2H, s, —CH$_2$O—), 5.53 (2H, s, =NCH$_2$—), 5.99 (2H, s, —OCH$_2$O—), 6.43 (1H, d, J=3.3 Hz, H-4'), 6.61 (1H, s, H-7), 6.76 (1H, d, J=3.3 Hz, H-3'), and 7.20–7.31 (6H, m, H-4, phenyl).

EXAMPLE 16

Synthesis of 1-Benzyl-3-(5'-methoxymethyl-2'-furyl)indazole

To a solution of 1-benzyl-3-(5'-hydroxymethyl-2'-furyl)indazole (0.2g, 0.66 mmole) dissolved in CH$_2$Cl$_2$ (5 mL) was added 1.0 M BCl$_3$/CH$_2$Cl$_2$ solution (1.5 mL) at −10±2° C. The mixture was allowed to react for 4 hours at this temperature. Then, methanol (5 mL) was added and the stirring continued for another 1 hour before quenched into ice water. The mixture was extracted with CH$_2$Cl$_2$, and the organic extract was neutralized by water wash, dried over anhydrous magnesium sulfate, evaporated for solvent removal, and purified by column chromatography (silica gel-benzene) to obtain 0.1 g 1-benzyl-3-(5'-methoxymethyl-2'-furyl)indazole in liquid in a yield of 50.0%.

MS (%), m/z: 318 (M$^+$). IR (KBr) $\gamma_{max}$: 1610 cm$^{-1}$(C-O). $^1$H-NMR (CDCl$_3$, 200 MHz) δ: 3.45 (3H, s, —CH$_2$OCH$_3$), 4.56 (3H, s, —CH$_2$OCH$_3$), 5.29 (2H, s, =NCH$_2$-), 6.52 (1H, d, J=3.3 Hz, H-4'), 6.91 (1H, d, J=3.3 Hz, H-3'), 7.18–7.36 (8H, m, H-5,6,7, phenyl), and 8.12 (1H, dd, J=8.1, 1.1 Hz, H-4).

EXAMPLE 17

Synthesis of 1-Benzyl-3-(5'-diethylaminomethyl-2'-furyl)indazole

To a solution of 1-benzyl-3-(5'-hydroxymethyl-2'-furyl)indazole (1.0 g, 3.3 mmole) dissolved in CH$_2$Cl$_2$ (50 mL) was added dropwise 1.0 M BCl$_3$/CH$_2$Cl$_2$ solution (20 mL) at −10±2° C. The mixture was allowed to react for 40 minutes at this temperature. Diethylamine (30 mL) was added, and the mixture was heated under reflux for 4 hours followed by quench into ice water. The mixture was extracted with CH$_2$Cl$_2$. The organic extract was neutralized by water wash, dried over anhydrous magnesium sulfate, and evaporated to leave a residue which upon purification by column chromatography (silica gel-benzene) afforded 0.1 6g 1-benzyl-3-(5'-diethylaminomethyl-2'-furyl)indazole in a yield of 39.0%.

MS (%), m/z: 359 (M$^+$). IR (KBr) $\gamma_{max}$: 1350 cm$^1$ (C-N). $^1$H-NMR (CDCl$_3$, 200 MHz) δ: 1.16 (6H, t, J=7.1 Hz, —N(CH$_2$CH$_3$)$_2$), 2.63 (4H, q, J=7.1 Hz, —N(CH$_2$CH$_3$)$_2$), 3.86 (2H, s, —CH$_2$N-), 5.64 (2H, s, =NCH$_2$—), 6.37 (1H, d, J=3.3 Hz, H-4'), 6.87 (1H, d, J=3.3 Hz, H-3'), 7.10–7.40 (8H, m, H-5,6,7, phenyl), and 8.10 (1H, d, J=8.2 Hz, H-4).

EXAMPLE 18

Synthesis of 1-Benzyl-3-(4'-ethoxycarbonylphenyl)indazole (a) To the mixture of anhydrous AlCl$_3$ (85 g, 0.64 mole) with dried toluene (90 mL) was added benzoyl chloride (50 mL, 0.43 mole) dropwise at 10±2° C. The mixture was warmed to 30±2° C. and stirred for 12 hours, and then heated to 100±5° C. and stirred for another 2 hr before it was cooled and added into ice water (200 mL) to terminate the reaction. The organic layer was separated and washed successively with water, 5% sodium carbonate and then water again till neutralized. The organic layer was dried over anhydrous magnesium sulfate and evaporated for solvent removal. The residue was recrystallized from n-hexane to obtain 62.1 g 4-methylbenzophenone in a yield 73.5%. mp: 55–57° C.

(b) To a mixture of 4-methylbenzophenone (25 g, 0.127 mole) with HOAc (130 mL) was added successively $CrO_3$ (35 g), $H_2O$ (80 mL) and conc. $H_2SO_4$ (25 mL). The mixture was heated for 3 hours at 100±5° C. and then quenched by adding ice water (500 mL) to yield a crude 4-benzoylbenzoic acid solid which was dissolved in a 10% KOH solution and filtered. The filtrate was acidified with diluted HCl to pH 2.0 and precipitate by subjected to ice bath. The precipitate was collected to obtain 21.3 g 4-benzoylbenzoic acid in a yield of 74.1%.

(c) A mixture of 4-benzoylbenzoic acid (20 g, 88.4 mmole), toluene (5 mL), p-toluenesulfonic acid (1 g) and ethanol (20 mL) was refluxed for 12 hours, cooled, washed with 5% sodium carbonate, and neutralized by water wash. The organic layer was dried over anhydrous magnesium sulfate and concentrated to obtain 22 g ethyl 4-benzoylbenzoate in a yield 90.5%.

(d) A mixture of ethyl 4-benzoylbenzoate (13.7 g, 54 mmole), benzylhydrazine (8 g, 65 mmole), ethanole (50 mL) and HOAc (1 mL) was refluxed for 12 hours and then treated with the procedure described in Example 1 to yield a crude product that was purified by column chromatography (silica gel-benzene), and recrystallized from n-hexane to give 4.8g 1-benzyl-3-(4'-ethoxycarbonylphenyl)indazole in a yield of 25.5%.

mp: 95–96° C. IR (KBr) $\gamma_{max}$: 1710, 1620cm$^{-1}$(C=O). MS (%), m/z: 356 (M$^+$). $^1$H-NMR (CDCl$_3$, 200 MHz) δ: 1.35 (3H, t, J=8.0 Hz, —CH$_2$CH$_3$), 4.35 (2H, q, J=8.0 Hz, —CH$_2$CH$_3$), 5.78 (2H, s, =NCH$_2$—), and 7.40–8.40 (13H, m, aromatic protons).

EXAMPLE 19

Synthesis of 1-Benzyl-3-(3'-ethoxycarbonylphenyl) indazole

3-Methylbenzophenone was treated sequentially with the procedures (a), (b), (c), and (d) in Example 18 to obtain, in the corresponding order, 3-benzoylbenzoic acid (yield: 72%), ethyl 3-benzoylbenzoate (yield: 86.3%), and 1-benzyl-3-(3'-ethoxycarbonylphenyl)indazole in a yield of 25.5%.

mp: 85–86° C. MS (%), m/z: 356 (M$^+$). IR (KBr) γmax: 1720, 1610 cm$^{-1}$(C=O). $^1$H-NMR (CDCl$_3$, 200 MHz) δ: 1.43 (3H, t, J=7.0 Hz, —CH$_2$CH$_3$), 4.44 (2H, q, J=7.0 Hz, —CH$_2$CH$_3$), 5.68 (2H, s, =NCH$_2$—), and 7.20–8.20 (13H, m, aromatic protons).

EXAMPLE 20

Synthesis of 1-Benzyl-3-(4'-hydroxycarbonylphenyl)indazole

To a solution of 1-benzyl-3-(4'-ethoxycarbonylphenyl) indazole (1 g, 2.8 mmole) dissolved in 10 mL methanol was added a sodium hydroxide solution (0.56 g in 20 mL water). After the mixture was heated under reflux for 6 hours, the methanol was removed by evaporation. The residue thus obtained was acidified with diluted HCl. After cooling in an ice bath, a solid precipitated and was collected to obtain 0.87 g 1-benzyl-3-(4'-hydroxycarbonyl-phenyl)-indazole in a yield of 94.5%.

mp: 205–207° C. MS (%), m/z: 328 (M$^+$). IR (KBr) $\gamma_{max}$: 3500–3300 cm$^{-1}$(OH) and 1700 cm, (C=O). $^1$H-NMR (DMSO-d$_6$, 200 MHz) δ: 5.77 (2H, s, =NCH$_2$—), 7.20–8.20 (13H, m, aromatic protons), and 13.0 (1H, br, —OH).

EXAMPLE 21

Synthesis of 1-benzyl-3-(3'-hydroxycarbonylphenyl) indazole

1-Benzyl-3-(3'-ethoxycarbonylphenyl)indazole (0.49 g, 0.11 mmole) was treated following the procedure described in Example 20 to obtain 0.83 g 1-benzyl-3-(3'-hydroxycarbonylphenyl)indazole in a yield of 90.2%.

mp: 190–192° C. MS (%), m/z: 328 (M$^+$). IR (KBr) $\gamma_{max}$: 3500–3300 cm$^{-1}$ (—OH) and 1700 cm$^{-1}$ (C=O). $^1$H-NMR (DMSO-d$_6$, 200 MHz) δ: 5.76 (2H, s, =NCH$_2$-), and 7.20–8.20 (13H, m, aromatic protons).

EXAMPLE 22

Synthesis of 1-Benzyl-3-(4'-hydroxymethylphenyl) indazole

1-Benzyl-3-(4'-ethoxycarbonylphenyl)indazole (0.4 g, 1.2 mmole) was treated following the procedure described in Example 12 to obtain 0.24 g 1-benzyl-3-(4'-hydroxymethylphenyl)indazole in a yield of 67.2%.

mp: 110–112° C. MS (%), m/z: 314 (M$^+$). IR (KBr) $\gamma_{max}$: 3300–2500 cm$^{-1}$(OH). $^1$H-NMR (DMSO-d6, 200 MHz) δ: 4.58 (2H, d, J=5.8 Hz, —CH$_2$O—), 5.31 (1H, t, J=5.2 Hz, —OH), 5.73 (2H, s, =NCH$_2$—), and 7.20–8.20 (13H, m, aromatic protons).

EXAMPLE 23

Synthesis of 1-Benzyl-3-(3'-hydroxymethylphenyl) indazole

1-Benzyl-3-(3'-ethoxycarbonylphenyl)indazole (0.4 g, 1.2 mmole) was treated following the procedure described in Example 12 to obtain 0.22 g 1-benzyl-3-(3'-hydroxymethylphenyl)indazole in a yield of 64.1 %.

mp: 98–99° C. MS (%), m/z: 314 (M$^+$). IR (KBr) $\gamma_{max}$: 3300–2500 cm$^{-1}$ (OH). $^1$H-NMR (DMSO-d$_6$, 200 MHz) δ: 4.78 (2H, s, —CH$_2$O—), 5.65 (2H, s, =NCH$_2$—), and 7.20–8.20 (13H, m, aromatic protons).

EXAMPLE 24

Synthesis of 1-Benzyl-3-(5'-methoxycarbonyl-2'-furyl)thieno[3,2-c]pyrazole (a) Synthesis of 5-Methoxycarbonyl-2-furyl 2'-thienyl ketone 2-Thiophenecarbonyl chloride (30.5 g, 0.21 mole), methyl 2-furoate (24 g, 0.19 mole), and anhydrous ferric chloride (0.42 g, 2.6 mmole) were allowed to react following the procedure described in Example 1 to obtain 28.7 g 5-methoxycarbonyl-2-furyl 2'-thienyl ketone in a yield of 63.8%.

mp: 103–106° C. MS (%), m/z: 236 (M$^+$). IR (KBr) $\gamma_{max}$: 1720, 1620cm$^{-1}$(C=O). 1H-NMR (CDCl$_3$, 200 MHz) δ: 3.98 (3H, s, —CH$_3$), 7.22–7.31 (2H, m, H-3,4), 7.41 (1H, d, J=3.5 Hz, H-4'), 7.76 (1H, d, J=3.5 Hz, H-3'), and 8.36 (1H, d, J=4.5 Hz, H-5).

(b) Synthesis of 1-Benzyl-3-(5'-methoxycarbonyl-2'-furyl) thieno[3,2-c]pyrazole

5-Methoxycarbonyl-2-furyl 2'-thienyl ketone (5.7 g, 0.024 mole) was used as the starting material and treated following the same procedure described in Example 1 to obtain 1.2 g 1-benzyl-3-(5'-methoxycarbonyl-2'-furyl)thieno [3,2-c]pyrazole in a yield of 14.8%.

mp: 142–143° C. MS (%), m/z: 338 (M$^+$). IR (KBr) $\gamma_{max}$: 1720 cm$^{-1}$(C=O). $^1$H-NMR (DMSO-d6, 200 MHz) δ: 3.85 (3H, s, —CH$_3$), 5.62 (2H, s, =NCH$_2$—), 6.92 (1H, d, J=3.5 Hz, H-3'), 7.24 (1H, d, J=4.8 Hz, H-6), 7.26–7.35 (5H, m, phenyl-H), 7.43 (1H, d, J=3.5 Hz, H-4'), and 7.77 (1H, dd, J=4.8, 1.5 Hz, H-5).

EXAMPLE 25

Synthesis of 1-Benzyl-3-(5'-hydroxycarbonyl-2'-furyl)thieno[3,2-c]pyrazole

1-Benzyl-3-(5'-methoxycarbonyl-2'-furyl)thieno[3,2-c] pyrazole (108 mg, 0.32 mmole) was treated following the procedure described in Example 6 to obtain 83.3 mg 1-benzyl-3-(5'-hydroxycarbonyl-2'-furyl)thieno[3,2-c] pyrazole in a yield of 80.3%.

mp: 221–224° C. MS (%), m/z: 324 (M$^+$). IR (KBr) $\gamma_{max}$: 3500 cm$^{-1}$(—OH), 1720 cm$^{-1}$(C=O). $^1$H-NMR (DMSO-d6, 200 MHz) δ: 5.62 (2H, s, =NCH$_2$—), 6.90 (1H, d, J=3.5 Hz, H-3'), 7.26 (1H, d, J=4.8 Hz, H-6), 7.25–7.35 (6H, m, H-4', phenyl), and 7.78 (1H, d, J=4.8 Hz, C5-H).

EXAMPLE 26

Synthesis of 1-Benzyl-3-(5'-hydroxymethyl-2'-furyl) thieno[3,2-c]pyrazole

1-Benzyl-3-(5'-methoxycarbonyl-2'-furyl)thieno[3,2-c] pyrazole (90 mg, 0.27 mole) was treated following the procedure described in Example 11 to obtain 63.4 mg 1-benzyl-3-(5'-hydroxymethyl-2'-furyl)thieno[3,2-c] pyrazole in a yield of 69.3%.

mp: 103–104° C. MS (%),m/z: 310 (M$^+$). IR (KBr) $\gamma_{max}$: 3360 cm$^{-1}$(—OH). $^1$H-NMR (DMSO-d$_6$, 200 MHz) δ: 4.46 (2H, d, J=5.3 Hz, —CH$_2$O—), 5.27 (1H, t, J=5.3 Hz, —OH), 5.55 (2H, s, =NCH$_2$—), 6.43 (1H, d, J=3.2 Hz, H-4'), 6.64 (1H, d, J=3.2 Hz, H-3'), 7.20 (1H, d, J=4.8 Hz, H-6), 7.27–7.35 (5H, m, phenyl-H), and 7.72 (1H. d, J=4.8 Hz, H-5).

EXAMPLE 27

Screening for Compounds Capable of Inhibiting Platelet Aggregation induced by PARs In vitro inhibitory activity of the fused pyrazolyl compounds was preliminarily evaluated by the following method: A platelet suspension in a Tyrode's solution was prepared according to a procedure described by Wu et al., *Br. J Pharm.*, 1995, 116: 1973–1978. The Tyrode's solution had the following composition (mM): NaCl (136.8), KCl (2.8), NaHCO$_3$ (11.9), MgCl$_2$ (1.1), NaH$_2$PO$_4$ (0.33), CaCl$_2$ (1.0), and glucose (11.2). The platelet number in the platelet suspension was adjusted to 4.5×10$^8$ platelets/mL with the aid of a Coulter Counter (Model ZM). Each compound to be tested was added to an aliquot of the platelet suspension, which was then incubated at 37° C. for 3 minutes under a stirring condition (1200 rpm) prior to addition of thrombin to activate PARs. Platelet aggregation was measured turbidimetrically with a light-ransmission aggremometer. The extent of platelet aggregation was determined at 5 minutes after the addition of thrombin. The percentage of aggregation was calculated by the method described in Teng et al., *Biochem. Biophys. Acta.*, 1987, 924: 375–382.

Compounds prepared in Examples 1–26 were tested and all showed inhibitory activity at different levels. For example, 1-benzyl-3-(5'-diethylaminomethyl)furyl-indazole unexpectedly showed much higher activity than a number of other compounds, e.g., 1-benzyl-3-(5'-hydroxymethyl)furyl-indazole. Further, 1-benzyl-3-(3'-ethoxycarbonyl)-phenyl-indazole showed activity at least 10 times that of several other tested compounds, e.g., 1-benzyl-3-(4'-ethoxycarbonyl)phenyl-indazole. It also unexpectedly exerted little or no effect on platelet activating factors other than PARs.

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of treating a disorder related to protease activated receptor-induced cell activation, comprising administering to a subject, in need thereof a compound having a pyrazolyl core; a first aryl group, via an alkylene linker, bonded to 1-N of the pyrazolyl core; a second aryl group fused at 4-C and 5-C of the pyrazolyl core; and a third aryl group bonded directly to 3-C of the pyrazolyl core; wherein each of the three aryl groups, independently, is phenyl, thienyl, furyl, or pyrrolyl, optionally substituted with halo, hydroxy, hydrothio, alkyl, alkoxy, alkylthio, (alkylthio)alkyl, carboxyl, alkoxycarbonyl, (thioalkyl) carbonyl, (alkylthio)carbonyl, aminocarbonyl, hydroxyalkyl, alkoxyalkyl, amino, aminoalkyl, thioalkyl, or alkylenedioxo; said compound being in an amount effective for treating the disorder.

2. The method of claim 1, wherein the compound is of the following formula:

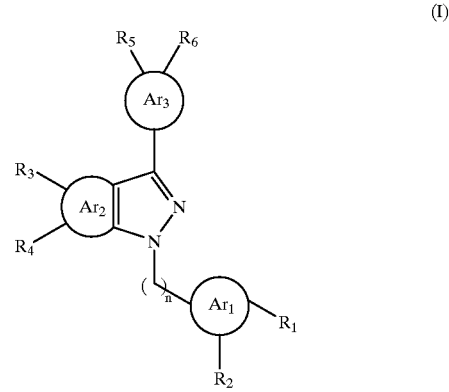

(I)

in which each of the first, second, and third aryl groups, Ar$_1$, Ar$_2$, and Ar$_3$, independently, is phenyl, thienyl, furyl, or pyrrolyl; each of R$_1$, R$_2$, R$_3$, R$_4$, R$_5$, and R$_6$, independently, is H, halo, —OR, —OH, —SR, —SH, —R, —C(=O)OH, —C(=O)OR, —C(=O)SH, —C(=O)SR, —C(=O)NRR', —ROH, —ROR', —RSR', —RSH, —NRR', —NHR, —NH$_2$, —RNR'R", —RNH$_2$, —RNHR', or —RSR', or R$_1$ and R$_2$ together, R$_3$ and R$_4$ together, or R$_5$ and R$_6$ together are —ORO—, wherein each of R, R', and R", independently, is C$_{1-4}$ alkyl; n is 1, or 2, or 3.

3. The method of claim 2, wherein $Ar_1$ is phenyl; $Ar_2$ is 6-substituted phenyl; and $Ar_3$ is 5'-substituted furyl or 3'-substituted phenyl.

4. The method of claim 2, wherein n is 1.

5. The method of claim 4, wherein $Ar_3$ is furyl and each of $R_5$ and $R_6$, independently, is H, halo, —R, —C(=O)OH, —C(=O)OR, —C(=O)SH, —C(=O)SR, —C(=O)NRR', —ROH, —ROR', —RSH, —NRR', —NHR, —NH$_2$, —RNR'R", —RNHR', —RNH$_2$, or —RSR', or $R_5$ and $R_6$ together are —ORO—.

6. The method of claim 4, wherein $Ar_3$ is phenyl and each of $R_5$ and $R_6$, independently, is H, halo, —R, —C(=O)OH, —C(=O)OR, —C(=O)SH, —C(=O)SR, —C(=O)NRR', —ROH, —ROR', —RSH, —NRR', —NHR, —NH$_2$, —RNR'R", —RNHR', —RNH$_2$, or —RSR', or $R_5$ and $R_6$ together are —ORO—.

7. The method of claim 6, wherein $Ar_3$ is phenyl, $R_5$ is H, and $R_6$ is at 4'—C.

8. The method of claim 6, wherein $Ar_3$ is phenyl, $R_5$ is at 4'—C, and $R_6$ is at 5'—C.

9. The method of claim 7, wherein $R_5$ is H, —C(=O)OH, —C(=O)OR, —C(=O)SH, —C(=O)SR, or —C(=O)NRR', and $R_6$ is H.

10. The method of claim 9, wherein $R_5$ is —C(=O)OR.

11. The method of claim 10, wherein $R_5$ is —C(=O)OEt.

12. The method of claim 11, wherein $Ar_2$ is phenyl and each of $R_3$ and $R_4$, independently, is H, halo, —R, —C(=O)OH, —C(=O)OR, —C(=O)SH, —C(=O)SR, —C(=O)NRR', —ROH, —ROR', —RSH, —NRR', —NHR, —NH$_2$, —RNR'R", —RNHR', —RNH$_2$, or —RSR', or $R_3$ and $R_4$ together are —ORO—.

13. The method of claim 12, wherein $Ar_1$ is phenyl and each of $R_1$ and $R_2$, independently, is H, halo, —R, —C(=O)OH, —C(=O)OR, —C(=O)SH, —C(=O)SR, —C(=O)NRR', —ROH, —ROR', —RSH, —NRR', —NHR, —RNR'R", —RNHR', or —RSR', or $R_1$ and $R_2$ together are —ORO—.

14. The method of claim 13, wherein each of $R_1$ and $R_2$ is H.

15. The method of claim 14, wherein $R_3$ is at 5—C and $R_4$ is at 6—C.

16. The method of claim 15, wherein each of $R_3$ and $R_4$ is H.

17. The method of claim 5, wherein $R_5$ is H and $R_6$ is at 5'—C.

18. The method of claim 17, wherein $R_6$ is —R, —ROH, —ROR', —RSH, —NH$_2$, —NRR', —NHR, —RNR'R", —RNHR', —RNH$_2$, or —RSR'.

19. The method of claim 18, wherein $Ar_1$ is phenyl and each of $R_1$ and $R_2$, independently, is H, halo, —R, —ROH, —ROR', —NH$_2$, —NRR', —RSR', —OR, —OH, —SR, or —SH.

20. The method of claim 18, wherein $Ar_2$ is phenyl, $R_3$ is at 5—C, and $R_4$ is at 6—C.

21. The method of claim 20, wherein $Ar_1$ is phenyl and each of $R_1$ and $R_2$, independently, is H, halo, —R, —ROH, —ROR', —NH$_2$, —NRR', —RSR', —OR, —OH, —SR, or —SH.

22. The method of claim 21, wherein each of $R_1$ and $R_2$ is H.

23. The method of claim 22, wherein $R_6$ is —CH$_2$OH.

24. The method of claim 23, wherein $R_3$ is H.

25. The method of claim 24, wherein $R_4$ is —CH$_3$.

26. The method of claim 24, wherein $R_4$ is —OCH$_3$.

27. The method of claim 22, wherein $R_6$ is —CH$_2$OCH$_3$.

28. The method of claim 27, wherein each of $R_3$ and $R_4$ is H.

29. The method of claim 22, wherein $R_6$ is —CH$_2$NEt$_2$.

30. The method of claim 29, wherein each of $R_3$ and $R_4$ is H.

* * * * *